United States Patent [19]

Whiteside et al.

[11] Patent Number: 4,731,086
[45] Date of Patent: Mar. 15, 1988

[54] SHIM FOR FEMORAL KNEE JOINT PROSTHESIS AND METHOD OF USING

[75] Inventors: Leo A. Whiteside, Chesterfield, Mo.; Walter P. Spires, Jr., Germantown, Tenn.

[73] Assignee: Dow Corning Wright, Arlington, Tenn.

[21] Appl. No.: 40,530

[22] Filed: Apr. 20, 1987

[51] Int. Cl.⁴ ............................................. A61F 2/38
[52] U.S. Cl. ..................................................... 623/20
[58] Field of Search ...................... 623/20, 18, 16, 22, 623/23

[56] References Cited

U.S. PATENT DOCUMENTS

| | | | |
|---|---|---|---|
| 3,683,421 | 8/1972 | Martinie | 623/23 |
| 4,224,696 | 9/1980 | Murray et al. | 623/20 |
| 4,224,697 | 9/1980 | Murray et al. | 623/20 |
| 4,257,129 | 3/1981 | Volz | 623/20 |
| 4,340,978 | 7/1982 | Buechel et al. | 623/20 |
| 4,417,571 | 11/1983 | Nelson et al. | 623/16 X |
| 4,563,778 | 1/1986 | Roche et al. | 623/22 |
| 4,568,348 | 2/1986 | Johnson et al. | 623/20 |

OTHER PUBLICATIONS

Brochure, "The P.C.A. TM Revision Total Knee System", Howmedica, Inc., Rutherford, N.J., No. H2030 3/83, 15M B, 1983, 62 pages.
Article, "Tibial Component Fixation in the Presence of Deficient Bone Stock", P. Brooks, P. S. Walker, and R. Scott, published for the 30th Annual ORS, Atlanta, Ga., Feb. 7-9, 1984, p. 106.
Product Catalog, "Townley Anatomic Total Knee Replacement", Depuy's 1979 Product Catalog, Warsaw, Ind., p. 1181.
Article, "Tibial Component Fixation in Deficient Tibial Bone Stock", P. Brooks, et al., [Clinical Orthopaedics and Related Research,] vol. 184, Apr. 1984, pp. 302-308.
"Whiteside Ortholoc Total Knee System", Surgical Procedure Booklet by Dow Corning Wright, (Form No. L095-0201), pp. 1-28, 1984.

*Primary Examiner*—Ronald L. Frinks
*Attorney, Agent, or Firm*—Susan M. Cornwall

[57] ABSTRACT

A prosthetic shim and a method for use of prosthetic shims to provide level support and increase the effective thickness of a femoral knee joint component having at least one fixation peg extending from the face which is to seat against the distal end of a femur. The shim is for placement between the femoral component and the femur and comprises a platform having a first surface to cooperatively engage the joint component face and a second surface to engage the distal end of the femur. The shim preferably has a means for securing the shim in place, such as spikes extending from the second surface to be driven into the femur. The platform preferably is shaped and dimensioned to be effective if placed centrally relative to the joint component face, covers a majority of the joint component face, and has an opening corresponding to each peg of the joint component so that the shim can be placed over each peg.

14 Claims, 5 Drawing Figures

SHIM FOR FEMORAL KNEE JOINT PROSTHESIS AND METHOD OF USING

BACKGROUND OF THE INVENTION

The present invention relates to prosthetic knee joints and more particularly to a device for and method of increasing the effective thickness of a femoral knee joint component.

Knee arthroplasty is becoming more common to partially or totally replace knee joints which have been damaged due to trauma or disease. In some cases, only one component of the knee joint, the tibial component or the femoral component, needs to be replaced, while, in other cases, both components of the knee joint need to be replaced. Knee arthroplasty requires that the end of the bone of the patient be cut and shaped to receive each component of the prosthesis in proper alignment and, thereafter, insuring that each component is properly sized to permit the repaired joint to function as normally as possible.

In some instances, the bone is so badly diseased or altered due to a previous knee implant that it requires that the bone be cut significantly in order to receive the prosthetic component. When this occurs and a typical knee joint is implanted, the leg will be shortened. One way surgeons avoid this problem is by implanting a thicker knee component to compensate for the lost bone. For example, some femoral component designs are available in various thicknesses for various sizes. For example, Howmedica, Inc. sells the P.C.A. Revision Total Knee System, which, as shown in Form #H2030 3/83 15M B (1983), has small, medium, and large femoral components, and the medium and large sizes are each available in two thicknesses. However, this solution requires the manufacturer to make and the surgeon to stock several joint components, to cover the various thicknesses and sizes to satisfy the patients' needs. This is a costly and cumbersome procedure for the surgeon and the manufacturer.

Another way for the surgeon to increase the effective joint thickness during knee arthroplasty is by using an implantable tibial base with removable tibial base insert. The tibial base insert may be of various thicknesses and be made to fit several sizes of tibial bases. The P.C.A. Revision Total Knee System is an example of such tibial components.

However, for either solution, using a thicker femoral component or a thicker tibial insert, an oversized component to compensate for loss bone could result in poor ligament balance, improper positioning of the joint line, and shifting of the patella position which could cause poor tracking of the patella on the femoral component. In addition, the surgeons that choose to use such knee prostheses are limited to the sizes supplied by the manufacturer and have no means of increasing the effective thickness beyond the thickest femoral component or tibial insert.

A third method some surgeons use to increase the effective length of the bone is to place a piece of bone between the cut end of the long bone and the knee component. This method has the disadvantages that the surgeons must acquire the bone material and carve the piece, and it most likely results in poor fit and fixation of the joint component.

It is known in the prosthetic art to incorporate cement spacers for controlling the thickness of cement applied between a prosthetic insert and a support member, such as an acetabulum. An example of such spacers is taught in U.S. Pat No. 4,417,571 to Nelson, et al. which discloses a prosthetic cement spacer and a method of using such spacers. One embodiment comprises a standoff body having a top surface and base surface and a means for anchoring the standoff body to the supporting member where the anchoring means extends outwardly from the base surface, e.g. a wire. The standoff body is preferably substantially cylindrical with a flat top surface, and the spacer is small enough to provide point support rather than a larger area support in order to be suitable for a variety of supporting bone shapes.

The method disclosed in Nelson, et al. comprises selecting a plurality (preferably at least three) of such spacers of desired height, positioning each against the supporting member by fully inserting the wires into the supporting member, filling the area between the supporting member and the prosthetic insert with cement, and placing the prosthetic insert against the outmost ends of the standoff bodies. This method is cumbersome and time consuming in that the surgeon must select several spacers, determine their placement, and attach each to the bone, one by one. Additionally, these spacers require that the surgeon take the time to apply and sculpture cement to fill in the space between the supporting member and the prosthesis.

Another example of spacers for controlling the thickness of cement are those shown in U.S. Pat. No. 4,563,778 to Roche, et al. which discloses a prosthetic acetabular cup of integral construction including a polyethylene liner in intimate contact with a metal shell and a plurality of standoff or spacer devices, preferably round or hemispherical in shape, that are securely located on the liner. Since the spacers are not removable, the surgeon has no flexibility in varying the height of the spacers, which are preferably sized to an overall height of 3 mm beyond the outer surface of the acetabulum cup to achieve optimum cement thickness.

The surgical procedure for using the spacers of Nelson, et al. and for inserting the acetabular cup assembly of Roche, et al. is to first prepare the acetabulum by reaming the bone surface to an increased spherical diameter to accommodate the additional height of the spacers. Therefore, the spacers and method disclosed do not teach a way of increasing the effective thickness of a knee joint component.

U.S. Pat. No. 3,683,421 to Martinie discloses a prosthetic hip joint assembly which is seated in the acetabulum opening. Martinie describes that the opening may be reamed out and provided with a plurality of grooves or cutouts 54 to more firmly hold the layer of acrylic 56 within which the socket assembly is mounted. Acrylic 56 appears to be cement that is typically applied just prior to inserting an socket assembly.

In the art there are known ways to patch proximal tibial defects when implanting the tibial component of a knee prosthesis; these ways are described in a paper entitled "Tibial Component Fixation in the Presence of Deficient Bone Stock" written by P. Brooks, P. S. Walker and R. Scott of Brigham & Women's Hospital in Boston, MA, and the V.A. Medical Center of West Roxbury. The article, published for the Feb. 7-9, 1984, 30th Annual ORS in Atlanta, Ga., shows that standard tibial trays can be supported on a defective tibia by (1) cement only, (2) cement, reinforced with two cancellous screws, (3) a Plexiglass (sic)—PLEXIGLAS ®, a trademark of the Rohm & Haas Co,—acrylic plastic spacer cemented into the defect, (4) a stainless steel spacer cemented into the defect, and (5) a custom made tray designed to match the defect. This teaching describes ways to patch bone defects but does not show a means for increasing the effective thickness of a knee joint component.

In DePuy's 1979 product catalog, an asymmetric tibial plateau formed of UHMWPE is shown as part of the Townley Anatomic Total Knee Replacement. This tibial plateau is asymmetric on its distal side shaped to fill in a portion where the proximal tibia is lacking. It is believed that this tibial plateau is attached to the cut end of the tibia by cementing it to the surface. This product provides a means of filling in a bone defect but does not provide a means for increasing the effective thickness of a knee joint component.

SUMMARY OF THE INVENTION

Objects of the present invention are to provide a device and method that allow a surgeon to increase the effective thickness of a femoral knee joint component to a desired degree that (1) is quick and easy to use, (2) is easy to manufacture, (3) can be designed to fit various femoral component designs and sizes, (4) is an optional element of the overall knee prosthesis, giving the surgeon the flexibility during surgery to use or not use it, (5) provides level support between the distal end of a femur and the femoral component, and (6) can be used with or without cement. Devices and methods meeting such objects would also have the advantage of minimizing the surgeons' and the manufacturers' inventory needs and costs of femoral components, since they would not need to stock components of various thicknesses.

The invention disclosed herein provides a prosthetic shim concept and a method for use of prosthetic shims to provide level support and increase the effective thickness of a femoral knee joint component. The invention provides for a femoral knee joint component having at least one peg extending from the face which is to seat against the distal end of a femur, the peg being insertable into the femur for fixation, a prosthetic shim for placement between the femoral component and the distal end of the femur for increasing the effective thickness of the femoral component. The shim comprises a platform having a first surface to cooperatively engage the femoral component face and a second surface to engage the distal end of the femur. The shim preferably has a means for securing the shim in place, such as spikes extending from the second surface to be driven into the bone. The platform preferably is shaped and dimensioned to be effective if placed centrally relative to the femoral component face, covers a majority of the femoral component face, and has an opening corresponding to each peg of the femoral component so that the shim can be placed over the pegs. Optionally, the platform has a reinforcing plate embedded therein and any surface of the shim can be contoured or formed from a material which enhances fixation to bone via bone ingrowth or fixation to the prosthesis or bone when using cement.

The invention further provides a method for using prosthetic shims to increase the effective thickness of a femoral knee joint component using the shims as described above. The method comprises (a) selecting a prosthetic shim of appropriate thickness to compensate for lost bone, (b) cooperatively engaging the prosthetic shim against the femoral component face, and (c) inserting the femoral component peg into the distal end of the femur until the shim engages the bone surface. This method anchors the femoral component to the bone with the shim positioned between the femoral component and the bone to provide level support and increase the effective thickness of the femoral component.

BRIEF DESCRIPTION OF THE DRAWINGS

The above and other objects and advantages of the present invention will become apparent to those skilled in the art upon an examination of the following description and drawings which are illustrative of the present invention.

In the Drawings

DETAILED DESCRIPTION OF THE INVENTION

Figure 1:
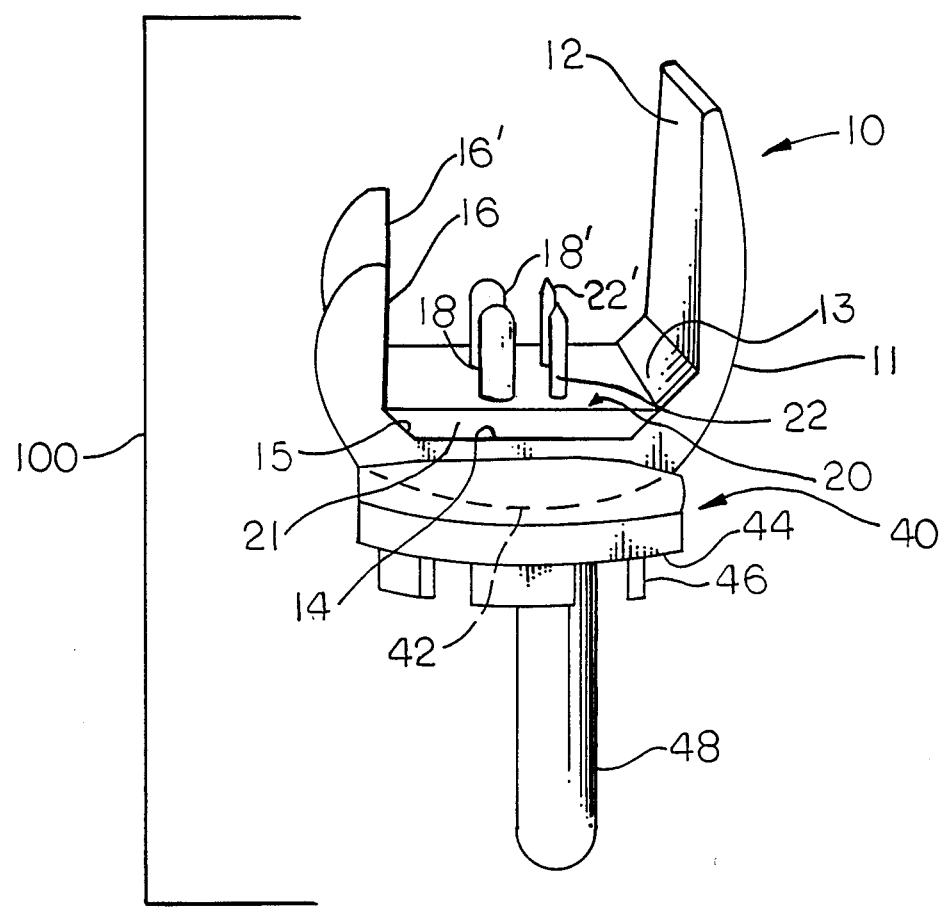
FIG. 1 is a perspective elevational view of total knee prosthesis 100 including prosthetic shim 20 according to the present invention.

Referring to the Drawings, wherein like reference characters designate corresponding parts throughout the Figures thereof, FIG. 1 depicts a total knee prosthesis 100 composed of femoral component 10, tibial component 40, and shim 20, shim 20 being a preferred form of the invention. The distal end of a femur (not shown) is resected and shaped to match the interior surfaces of femoral component 10 with shim 20 placed therein. Fixation of femoral component 10 is achieved by inserting fixation pegs 18 and 18' into the distal end of the femur. Tibial component 40 is designed to fit on the proximal end of a tibia (not shown) which has been shaped to match the bottom surface 44 of tibial component 40. Anchoring of tibial component 40 is achieved by inserting stem 48 and peripheral pegs, one of which is shown as 46, into the proximal end of the tibia. Once the two joint components are implanted, outside surface 11 of femoral component 10 contacts upper surface 42 of tibial component 40, thereby permitting articulation of the knee joint prosthesis.

The interior surfaces of femoral component 10 consists of anterior flat surface 12, anterior bevel surface 13, bottom face 14, posterior bevel surface 15, and posterior flat surfaces 16 and 16'. Fixation pegs 18 and 18' extend from bottom face 14. Once assembled, shim 20 is resting on top of bottom face 14 and provides the means for increasing the effective thickness of femoral component 10 once the femoral component is attached to the resected femur. Shim 20 comprises platform 21 which has top surface 24 and bottom surface 32, and openings 26 and 26' through which fixation pegs 18 and 18' are inserted. Fixation spikes 22 and 22' extend upward from top surface 24 of platform 21 anterior to openings 26 and 26' for insertion into the femur for fixation.

Figure 2:
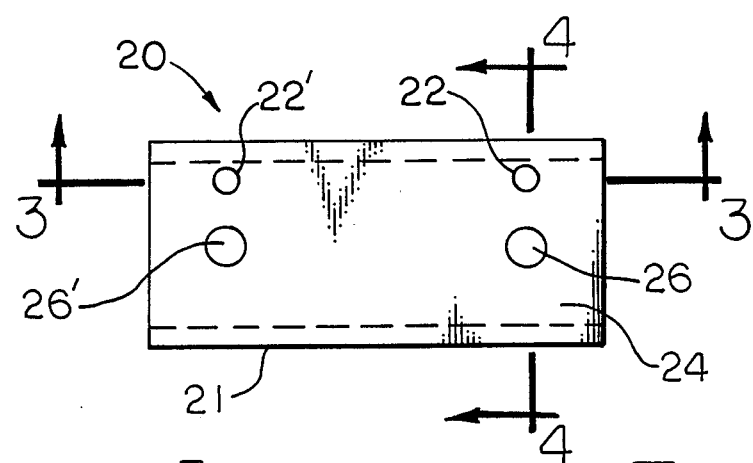
FIG. 2 is a top view of prosthetic shim 20.
Figure 3:
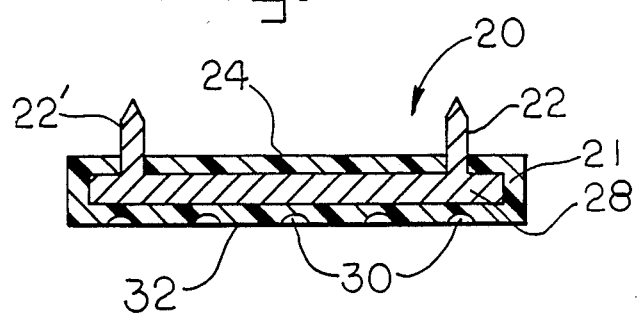
FIG. 3 is a side elevational view of prosthetic shim 20 in partial cross-section taken along lines 3—3 of FIG. 2.
Figure 4:
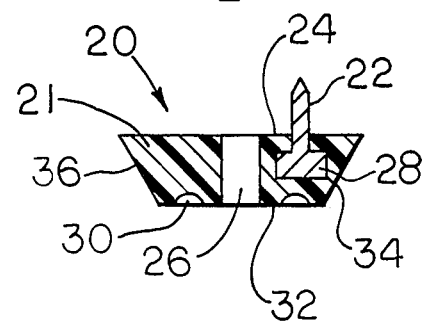
FIG. 4 is a side elevational view of prosthetic shim 20 in partial cross-section taken along lines 4—4 of FIG. 2.
Figure 5:
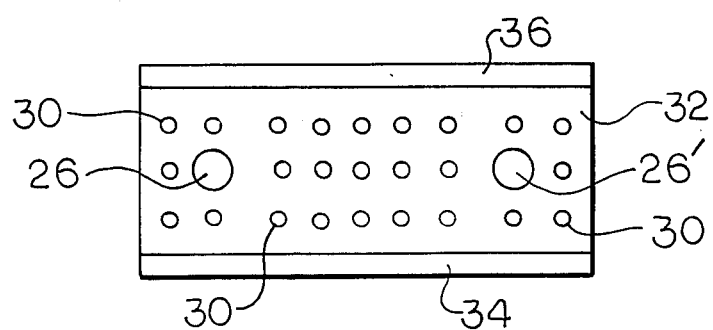
FIG. 5 is a bottom view of prosthetic shim 20.

Platform 20 has a reinforcing plate 28 embedded therein, as best can be seen in FIGS. 3 and 4 which are cross-sectional views of shim 20 taken along lines 3—3 and 4—4 of FIG. 2, respectively. In bottom surface 32 of platform 21, there are bores 30 which extend partially into platform 21 and are present to improve cement fixation to femoral component 10, if cement is used. Although not shown, top surface 24 or any other surface may be contoured to improve fixation.

FIG. 4 best illustrates that the shape of platform 21 is made to correspond to the inner surfaces of femoral component 10. The incline of anterior side surface 34 of platform 21 corresponds to anterior bevel surface 13 of femoral component 10, and the incline of posterior side surface 36 of platform 21 corresponds to posterior bevel surface 15 of femoral component 10. Because of the shape and dimensions of shim 20, it cooperatively engages femoral component 10.

During one implantation procedure of femoral component 10 with prosthetic shim 20, shim 20 is placed against bottom face 14 on femoral component 10 by inserting pegs 18 and 18' of femoral component 10 through corresponding openings 26 and 26' of shim 20. The location of openings 26 and 26' which correspond with pegs 18 and 18' helps insure proper placement of shim 20 on surface 10, thereby making assembly easier for the surgeon. The distal end of the femur is resected and shaped to fit inside femoral component 10 with shim 20 therein. Femoral component 10 with shim 20 is then placed on and anchored to the femur by inserting pegs 18 and 18' and spikes 22 and 22' into the femur. Cement may be used between femoral component 10 and the bone and/or between shim 20 and femoral component 10.

Alternatively, shim 20 may be anchored first to the cut and shaped femur and then femoral component 10 attached to the femur by inserting pegs 18 and 18' through openings 26 and 26' and into the distal femur. In either implantation procedure, a shim of appropriate thickness is selected to compensate for the lost bone.

The platform may be made of various biocompatible materials, such as polymethylmethacrylate which has the further advantage of eliminating of an interface between the platform and polymethylmethacrylate bone cement, if cement is used, since stresses are known to concentrate at the interface and cause failure. Other materials that can be used to form the platform are hydroxyapatite type materials, metals, composites, and bone allograft. The reinforcing plate and the spikes may be made of titanium alloy, a biocompatible material which is well known in the art.

The shim may comprise more than one platform, one on top of another. However it is preferred, for ease of use during surgery, to use a single piece shim. Preferably, the shim is generally centrally located relative to the face of the femoral component and covers a majority of the face of the femoral component. The platform surface facing the bone can be asymmetric to fill in defects in the bone.

These and other variations of the present invention may be made which fall within the scope of the appended claims even though such variations were not specifically discussed above.

That which is claimed is:

1. For an implantable femoral knee joint component having a face which is to seat against the distal end of a femur and a peg extending from said joint component face, said peg being insertable into said distal end of said femur, a prosthetic shim for placement between said joint component and said femur for increasing the effective thickness of said joint component, said shim comprising:
    a platform having a first surface to cooperatively engage said joint component face and a second surface to engage said distal end of said femur to provide level support and increase the effective thickness of said joint component.

2. A prosthetic shim as defined in claim 1 further comprising a means for securing said shim in place between said joint component face and said femur.

3. A prosthetic shim as defined in claim 2 wherein said securing means comprises a spike extending from said second surface wherein said spike is to be driven into said femur.

4. A prosthetic shim as defined in claim 1 wherein said platform has a shape and dimensions for generally central placement relative to said joint component face.

5. A prosthetic shim as defined in claim 1 wherein said platform has a shape and dimensions for covering a majority of said joint component face.

6. A prosthetic shim as defined in claim 1 wherein said platform has an opening extending therethrough corresponding to said peg on said joint component.

7. A prosthetic shim as defined in claim 1 wherein said platform contains a reinforcing plate embedded therein.

8. A method of increasing the effective thickness of an implantable femoral knee joint component having a face which is to seat against the distal end of a femur and a peg extending from said joint component face, said peg being insertable into said distal end of said femur, comprising the steps of:
    (a) selecting a prosthetic shim of appropriate thickness, said shim comprising a platform having a first surface to cooperatively engage said joint component face and a second surface to engage said distal end of said femur,
    (b) placing said selected prosthetic shim against said joint component face,
    (c) inserting said joint component peg into said distal end of said femur until said second surface of said shim engages said femur thereby anchoring said joint component to said femur with said shim between said joint component and said distal end of said femur to provide level support and increase the effective thickness of said joint component.

9. A method as defined in claim 8 wherein said shim further comprises a means for securing said shim in place between said joint component and said femur.

10. A method as defined in claim 9 wherein said securing means comprises a spike extending from said second surface wherein said spike is to be driven into said femur.

11. A method as defined in claim 8 wherein said shim is placed generally centrally on said joint component face.

12. A method as defined in claim 8 wherein said platform has a shape and dimensions for covering a majority of said joint component face.

13. A method as defined in claim 8 wherein said platform has an opening extending therethrough corresponding to said peg on said joint component.

14. A method as defined in claim 8 wherein said platform contains a reinforcing plate embedded therein.

* * * * *